US009968084B2

(12) United States Patent
Mann et al.

(10) Patent No.: US 9,968,084 B2
(45) Date of Patent: May 15, 2018

(54) SYNERGISTIC HERBICIDAL COMPOSITION CONTAINING PENOXSULAM, TRICLOPYR AND IMAZETHAPYR

(75) Inventors: Richard K. Mann, Franklin, IN (US); Monica Sorribas Amela, Indianapolis, IN (US); Charles Simpson, Greenville, MS (US); Andrew T. Ellis, Greenville, MS (US); Jonathan D. Siebert, Greenville, MS (US); Ralph B. Lassiter, Jr., Little Rock, AR (US); Larry Walton, Tupelo, MS (US); Vernon Langston, The Woodlands, TX (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days. days.

(21) Appl. No.: 13/351,652

(22) Filed: Jan. 17, 2012

(65) Prior Publication Data
US 2012/0184437 A1 Jul. 19, 2012

Related U.S. Application Data

(60) Provisional application No. 61/433,612, filed on Jan. 18, 2011.

(51) Int. Cl.
A01N 43/40 (2006.01)
A01N 43/90 (2006.01)

(52) U.S. Cl.
CPC ............. *A01N 43/40* (2013.01); *A01N 43/90* (2013.01)

(58) Field of Classification Search
None
See application file for complete search history.

(56) References Cited

U.S. PATENT DOCUMENTS

| | | |
|---|---|---|
| 5,858,924 A | 1/1999 | Johnson et al. |
| 2002/0055435 A1 | 5/2002 | Baltruschat et al. |
| 2005/0250647 A1 | 11/2005 | Hills et al. |
| 2006/0183637 A1 | 8/2006 | Loughner et al. |
| 2007/0197391 A1 | 8/2007 | Clark et al. |
| 2008/0227637 A1 | 9/2008 | Guice et al. |
| 2009/0062121 A1* | 3/2009 | Satchivi et al. ............ 504/105 |
| 2009/0298691 A1* | 12/2009 | Koschnick et al. ......... 504/121 |
| 2009/0325803 A1 | 12/2009 | Koschnick |
| 2010/0279864 A1 | 11/2010 | Mann et al. |
| 2011/0092366 A1 | 4/2011 | Griveau et al. |
| 2011/0098182 A1 | 4/2011 | Mann et al. |

OTHER PUBLICATIONS

GRASP XTRA Label (published on Oct. 8, 2009).*
Disclosed Anonymously 462055: "2-(2,2-difluoroethoxy)-6-trifluoromethy1-N-(5,8-dimethoxy[1,2,4]triazolo[1,5-c]pyrimidin-2-y1)benzenesfulfonamide and its use as a herbicide in mixtures" Research Disclosure, Oct. 2002, pp. 1832-1833.
"Penoxsulam and Its Use as a Herbicide in Mixtures for Use in Rice, Wheat, Barely, Oats, Sorghum, Corn, Maize, Ivm, Rangeland Pastures, Grasslands, Fallowland, Turf, and Aquatics" The IP.com Journal, vol. 5, No. 4, Apr. 2005, pp. 286-293.

* cited by examiner

*Primary Examiner* — Mina Haghighatian
*Assistant Examiner* — Mei Ping Chui
(74) *Attorney, Agent, or Firm* — Michael R. Asam

(57) ABSTRACT

An synergistic herbicidal composition containing penoxsulam plus triclopyr and imazethapyr or imazamox for controlling weeds in crops, especially rice, cereal and grain crops, pastures, rangelands, industrial vegetation management (IVM), aquatics and turf. These compositions provide improved post-emergence herbicidal weed control.

5 Claims, No Drawings

US 9,968,084 B2

SYNERGISTIC HERBICIDAL COMPOSITION CONTAINING PENOXSULAM, TRICLOPYR AND IMAZETHAPYR

CROSS REFERENCE TO RELATED APPLICATIONS

This application claims the benefit of U.S. Provisional Patent Application Ser. No. 61/433,612 filed Jan. 18, 2011.

FIELD OF THE INVENTION

This invention concerns a synergistic herbicidal composition containing penoxsulam plus triclopyr and imazethapyr or imazamox for controlling weeds in crops, especially rice, cereal and grain crops, pastures, rangelands, industrial vegetation management (IVM), aquatics and turf. These compositions particularly provide improved post-emergence herbicidal weed control.

BACKGROUND OF THE INVENTION

The protection of crops from weeds and other vegetation which inhibit crop growth is a constantly recurring problem in agriculture. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use.

In some cases, herbicidal active ingredients have been shown to be more effective in combination than when applied individually and this is referred to as "synergism." As described in the *Herbicide Handbook* of the Weed Science Society of America, Ninth Edition, 2007, p. 429 "'synergism' [is] an interaction of two or more factors such that the effect when combined is greater than the predicted effect based on the response to each factor applied separately." The present invention is based on the discovery that penoxsulam, triclopyr and imazethapyr or imazamox, already known individually for their herbicidal efficacy, display a synergistic effect when applied in combination.

SUMMARY OF THE INVENTION

The present invention concerns a synergistic herbicidal mixture comprising an herbicidally effective amount of (a) penoxsulam plus triclopyr and (b) imazethapyr or imazamox. The compositions may also contain an agriculturally acceptable adjuvant and/or carrier.

The present invention also concerns herbicidal compositions for and methods of controlling the growth of undesirable vegetation, particularly in monocot crops including rice, wheat, barley, oats, rye, sorghum, corn, maize, pastures, grasslands, rangelands, fallowland, turf, IVM and aquatics and the use of these synergistic compositions.

The species spectra of acetolactate synthase (ALS) inhibitors like penoxsulam and imazethapyr, i.e., the weed species which the respective compounds control, are broad and highly complementary with that of triclopyr. For example, it has been surprisingly found that a combination of penoxsulam, triclopyr and imazethapyr exhibits a synergistic action in the control of barnyardgrass (*Echinochloa crus-galli*; ECHCG) and foxtail (*Setaria* spp., SETSS) at application rates equal to or lower than the rates of the individual compounds.

The species spectra of acetolactate synthase (ALS) inhibitors like penoxsulam and imazamox, i.e., the weed species which the respective compounds control, are broad and highly complementary with that of triclopyr. For example, it has been surprisingly found that a combination of penoxsulam, triclopyr and imazamox exhibits a synergistic action in the control of barnyardgrass (*Echinochloa crus-galli*; ECHCG), broadleaf signalgrass (*Brachiaria platyphylla* (GRISEB.) NASH; BRAPP) and Texasweed (*Caperonia palustris* ST.-HIL.; CNPPA) at application rates equal to or lower than the rates of the individual compounds.

DETAILED DESCRIPTION OF THE INVENTION

Penoxsulam is the common name for 2-(2,2-difluoroethoxy)-N-(5,8-dimethoxy-[1,2,4]-triazolo[1,5-c]pyrimidin-2-yl)-6-(trifluoromethyl)benzenesulfonamide. Its herbicidal activity is described in *The Pesticide Manual*, Fifteenth Edition, 2009. Penoxsulam controls *Echinochloa* spp., as well as many broadleaf, sedge and aquatic weeds in rice, and *Apera* spp. a grass, as well as many broadleaf weeds in cereals.

Triclopyr is the common name for 2-[(3,5,6-trichloro-2-pyridinyl)oxy]acetic acid. Its herbicidal activity is described in *The Pesticide Manual*, Fifteenth Edition, 2009. Triclopyr controls a wide range of woody plants and broadleaf weeds. It can be used as the acid itself or as an agriculturally acceptable salt or ester. Use as the butotyl ester or the triethylammonium salt is preferred, with use as the triethylammonium salt being most preferred.

Imazethapyr is the common name for 2-[4,5-dihydro-4-methyl-4-(1-methylethyl)-5-oxo-1H-imidazol-2-yl]-5-ethyl-3-pyridinecarboxylic acid. Its herbicidal activity is described in *The Pesticide Manual*, Fifteenth Edition, 2009. Imazethapyr controls many annual and perennial grass and broadleaf weeds in alfalfa, peas, beans, soybeans and imidazolinone tolerant rice and corn. Use as the acid or the ammonium salt is preferred with use as the ammonium salt being most preferred.

Imazamox is the common name for 2-[4,5-dihydro-4-methyl-4-(1-methylethyl)-5-oxo-1H-imidazol-2-yl]-5-(methoxymethyl)-3-pyridinecarboxylic acid. Its herbicidal activity is described in *The Pesticide Manual*, Fifteenth Edition, 2009. Imazamox controls many annual and perennial grass and broadleaf weeds in corn, rape, alfalfa, peas, beans, and imidazolinone tolerant rice, wheat, rape and sunflowers. Use as the acid or the ammonium salt is preferred with use as the ammonium salt being most preferred.

The term herbicide is used herein to mean an active ingredient that kills, controls or otherwise adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation include germinant seeds, emerging seedlings, plants emerging from vegetative propagules, and established vegetation.

Herbicidal activity is exhibited by the compounds of the synergistic mixture when they are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, it is preferred to apply the composition of the present invention postemergence to relatively immature undesirable vegetation to achieve the maximum control of weeds.

For the most preferred triethylammonium salt of triclopyr, an acid equivalent (g ae) is equal to (0.717×g active ingredient). As an example, 250 grams active ingredient is equal to 179.3 grams acid equivalent.

For the most preferred ammonium salt of imazethapyr, an acid equivalent (g ae) is equal to (0.944×g active ingredient). As an example, 250 grams active ingredient is equal to 236 grams acid equivalent.

For the most preferred ammonium salt of imazamox, an acid equivalent (g ae) is equal to (0.944×g active ingredient). As an example, 250 grams active ingredient is equal to 236 grams acid equivalent.

In the composition of this invention, the weight ratio of penoxsulam (active ingredient) plus triclopyr (active ingredient) to imazethapyr (active ingredient) at which the herbicidal effect is synergistic lies within the range from about 1:1 to about 17:1.

The rate at which the synergistic composition is applied will depend upon the particular type of weed to be controlled, the degree of control required, and the timing and method of application. The ALS inhibitor herbicide imazethapyr is applied at a rate from about 30 g ai/ha to about 90 g ai/ha (28.3 and 84.9 g ae/ha) and penoxsulam plus triclopyr is applied at a rate from about 110 g ai/ha to about 500 g ai/ha. Penoxsulam is applied at a rate from 10 to 50 g ai/ha, and triclopyr is applied at a rate from 100 to 450 g ai/ha (72 and 323 g ae/ha). The ALS inhibitor herbicide imazamox is applied at a rate from about 30 g ai/ha to about 70 g ai/ha (28.3 and 66.1 g ae/ha) and penoxsulam plus triclopyr is applied at a rate from about 110 g ai/ha to about 500 g ai/ha. Penoxsulam is applied at a rate from 10 to 50 g ai/ha, and triclopyr is applied at a rate from 100 to 450 g ai/ha (72 and 323 g ae/ha).

The components of the synergistic mixture of the present invention can be applied either separately or as part of a multipart herbicidal system, which can be provided as a premix or a tank mix.

The synergistic mixture of the present invention can be applied in conjunction with one or more other herbicides to control a wider variety of undesirable vegetation. When used in conjunction with other herbicides, the composition can be formulated with the other herbicide or herbicides, tank mixed with the other herbicide or herbicides or applied sequentially with the other herbicide or herbicides. Some of the herbicides that can be employed in conjunction with the synergistic composition of the present invention include: 2,4-D, acetochlor, acifluorfen, aclonifen, AE0172747, alachlor, amidosulfuron, aminotriazole, ammonium thiocyanate, anilifos, atrazine, AVH 301, azimsulfuron, benfuresate, bensulfuron-methyl, bentazone, benthiocarb, benzobicyclon, bifenox, bispyribac-sodium, bromacil, bromoxynil, butachlor, butafenacil, butralin, cafenstrole, carbetamide, carfentrazone-ethyl, chlorflurenol, chlorimuron, chlorpropham, cinosulfuron, clethodim, clomazone, clopyralid, cloransulam-methyl, cyclosulfamuron, cycloxydim, cyhalofop-butyl, dicamba, dichlobenil, dichlorprop-P, diclosulam, diflufenican, diflufenzopyr, dimethenamid, dimethenamid-p, diquat, dithiopyr, diuron, EK2612, EPTC, esprocarb, ET-751, ethoxysulfuron, ethbenzanid, F7967, fenoxaprop, fenoxaprop-ethyl, fenoxaprop-ethyl+isoxadifen-ethyl, fentrazamide, flazasulfuron, florasulam, fluazifop, fluazifop-P-butyl, flucetosulfuron (LGC-42153), flufenacet, flufenpyr-ethyl, flumetsulam, flumiclorac-pentyl, flumioxazin, fluometuron, flupyrsulfuron, fluoroxypyr, fomesafen, foramsulfuron, fumiclorac, glufosinate, glufosinate-ammonium, glyphosate, halosulfuron-methyl, haloxyfop-methyl, haloxyfop-R, imazamethabenz, imazapic, imazapyr, imazaquin, imazosulfuron, indanofan, indaziflam, iodosulfuron, ioxynil, ipfencarbazone (HOK-201), IR 5790, isoproturon, isoxaben, isoxaflutole, KUH-071, lactofen, linuron, MCPA, MCPA ester & amine, mecoprop-P, mefenacet, mesosulfuron, mesotrione, metamifop, metazosulfuron (NC-620), metolachlor, metosulam, metribuzin, metsulfuron, molinate, MSMA, napropamide, nicosulfuron, norflurazon, OK-9701, orthosulfamuron, oryzalin, oxadiargyl, oxadiazon, oxazichlomefone, oxyfluorfen, paraquat, pendimethalin, pentoxazone, pethoxamid, picloram, picolinafen, piperophos, pretilachlor, primisulfuron, profoxydim, propachlor, propanil, propyrisulfuron (TH-547), propyzamide, prosulfocarb, prosulfuron, pyraclonil, pyrazogyl, pyrazosulfuron, pyribenzoxim (LGC-40863), pyriftalid, pyriminobac-methyl, pyrimisulfan (KUH-021), pyroxsulam, pyroxasulfone (KIH-485), quinclorac, quizalofop-ethyl-D, S-3252, sethoxydim, simazine, SL-0401, SL-0402, S-metolachlor, sulcotrione, sulfentrazone, sulfosate, tebuthiuron, tefuryltrione (AVH-301), terbacil, thiazopyr, thiobencarb, trifluralin and tritosulfuron.

The synergistic composition of the present invention can, further, be used in conjunction with glyphosate, glufosinate, dicamba, imidazolinones, sulfonylureas, or 2,4-D on glyphosate-tolerant, glufosinate-tolerant, dicamba-tolerant, imidazolinone-tolerant, sulfonylurea-tolerant and 2,4-D-tolerant crops. It is generally preferred to use the synergistic composition of the present invention in combination with herbicides that are selective for the crop being treated and which complement the spectrum of weeds controlled by these compounds at the application rate employed. It is further generally preferred to apply the synergistic composition of the present invention and other complementary herbicides at the same time, either as a combination formulation or as a tank mix.

The synergistic composition of the present invention can generally be employed in combination with known herbicide safeners, such as benoxacor, benthiocarb, brassinolide, cloquintocet (mexyl), cyometrinil, daimuron, dichlormid, dicyclonon, dimepiperate, disulfoton, fenchlorazole-ethyl, fenclorim, flurazole, fluxofenim, furilazole, harpin proteins, isoxadifen-ethyl, mefenpyr-diethyl, MG 191, MON 4660, naphthalic anhydride (NA), oxabetrinil, R29148 and N-phenyl-sulfonylbenzoic acid amides, to enhance their selectivity.

In practice, it is preferable to use the synergistic composition of the present invention in mixtures containing an herbicidally effective amount of the herbicidal components along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with herbicidal components or other composition ingredients. Such mixtures can be designed for application directly to weeds or their locus or can be concentrates or formulations that are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art. Some of these adjuvants include, but are not limited to, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. Water is generally the carrier of choice for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, and the like.

It is usually desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Surfactants conventionally used in the art of formulation and which may also be used in the present formulations are described, inter alia, in "McCutcheon's Detergents and Emulsifiers Annual," MC Publishing Corp., Ridgewood, N.J., 1998 and in "Encyclopedia of Surfactants," Vol. I-III, Chemical Publishing Co., New York, 1980-81. Typical surface-active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutyl-naphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable or seed oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, particulary methyl esters.

Oftentimes, some of these materials, such as vegetable or seed oils and their esters, can be used interchangeably as an agricultural adjuvant, as a liquid carrier or as a surface active agent.

Other additives commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of the active ingredients in the synergistic composition of the present invention is generally from 0.001 to 98 percent by weight. Concentrations from 0.01 to 90 percent by weight are often employed. In compositions designed to be employed as concentrates, the active ingredients are generally present in a concentration from 1 to 98 weight percent, preferably 5 to 90 weight percent. Such compositions are typically diluted with an inert carrier, such as water, before application, or applied as a dry or liquid formulation directly into flooded rice fields. The diluted compositions usually applied to weeds or the locus of weeds generally contain 0.0001 to 10 weight percent active ingredient and preferably contain 0.001 to 5.0 weight percent.

The present compositions can be applied to weeds or their locus by the use of conventional ground or aerial dusters, sprayers, and granule applicators, by addition to irrigation or paddy water, and by other conventional means known to those skilled in the art.

The following examples illustrate the present invention. Evaluation of Postemergence Herbicidal Activity of Mixtures in the Field Field trials were conducted in rice using standard herbicide small plot research methodology. Plot size was 2×6 meter (m) with 4 replicates per treatment. The rice crop was grown using normal cultural practices for fertilization, seeding, watering, flooding and maintenance to ensure good growth of the crop and the weeds.

All treatments in the field trials were applied using a compressed air backpack sprayer calibrated to apply 187 liters per hectare (L/ha) spray volume. Commercially available products of the premix penoxsulam plus triclopyr (GraspXTRA® herbicide, trademark of Dow AgroSciences LLC) and imazethapyr or imazamox were mixed in water at appropriately formulated product rates to achieve the desired rates based on a unit area of application (hectare) to achieve the desired rates as shown. The GraspXTRA herbicide is a product that contains 0.25 lb penoxulam and 2.06 lb triclopyr triethylamine salt (1.5 lb acid equivalent) per gallon, so the weight ratio of the penoxulam to triclopyr acid equivalent is 1:6. Imazethapyr was used as Newpath 240 SL. imazamox was used as Beyond 120 SL. Treatments were rated at 15 to 63 days after application as compared to the untreated control plants. Visual weed control was scored on a scale of 0 to 100 percent where 0 corresponds to no injury and 100 corresponds to complete kill.

Tables 1 and 2 demonstrate the herbicidal synergistic efficacy of penoxsulam+triclopyr tank mixed with imazethapyr on weed control. Table 3 demonstrates the herbicidal synergistic efficacy of penoxsulam+triclopyr tank mixed with imazamox on weed control. All treatment results, both for the single premix product, the single entity product and mixtures, are an average of 4 replicates and the tank mix interactions are significant at the P>0.05 level.

Colby's equation was used to determine the herbicidal effects expected from the mixtures (Colby, S. R. Calculation of the synergistic and antagonistic response of herbicide combinations. *Weeds* 1967, 15, 20-22.).

The following equation was used to calculate the expected activity of mixtures containing two active ingredients, A and B:

Expected=$A+B-(A \times B/100)$

A=observed efficacy of active ingredient A at the same concentration as used in the mixture.

B=observed efficacy of active ingredient B at the same concentration as used in the mixture.

Compounds tested, application rates employed, plant species tested, and results are given in Tables 1-3. All comparisons are an average of 4 replicates and are significant at the P>0.05 level. Rates of penoxsulam, triclopyr and imazethapyr or imazamox are expressed in grams active ingredient/hectare (g ai/ha).

TABLE 1

Synergistic Activity of Herbicidal Compositions of Penoxsulam Plus Triclopyr tank mixed with Imazethapyr on grass weed (*Echinochloa crus-galli* (ECHCG)) control in the field.

| Application Rates | | % Control 15DAA | | % Control 63DAA | |
| --- | --- | --- | --- | --- | --- |
| Penoxsulam + Triclopyr (g ai/ha) | Imazethapyr (g ai/ha) | ECHCG | | ECHCG | |
| | | Ob | Ex | Ob | Ex |
| 327 | 0 | 44 | — | 9 | — |
| 0 | 70 | 69 | — | 36 | — |
| 327 | 70 | 94 | 82 | 93 | 42 |
| 373 | 0 | 53 | — | 15 | — |
| 0 | 70 | 69 | — | 36 | — |
| 373 | 70 | 96 | 85 | 93 | 46 |

TABLE 2

Synergistic Activity of Herbicidal Compositions of Penoxsulam Plus Triclopyr tank mixed with Imazethapyr on grass weed (*Setaria* spp. (SETSS)) control in the field.

| Application Rates | | % Control 15DAA | | % Control 63DAA | |
| --- | --- | --- | --- | --- | --- |
| Penoxsulam + Triclopyr (g ai/ha) | Imazethapyr (g ai/ha) | SETSS | | SETSS | |
| | | Ob | Ex | Ob | Ex |
| 327 | 0 | 44 | — | 15 | — |
| 0 | 70 | 69 | — | 36 | — |
| 327 | 70 | 93 | 83 | 93 | 42 |
| 373 | 0 | 53 | — | 15 | — |
| 0 | 70 | 69 | — | 36 | — |
| 373 | 70 | 96 | 85 | 93 | 46 |

TABLE 3

Synergistic Activity of Herbicidal Compositions of Penoxsulam Plus Triclopyr tank mixed with Imazamox on grass weeds (*Echinochloa crus-galli* (ECHCG), *Brachiaria platyphylla* (GRISEB.) NASH (BRAPP), and *Caperonia palustris* ST.-HIL. (CNPPA)) control in the field.

| Application Rates (g ai/ha) | | % Control 43 DAA | | % Control 41 DAA | | % Control 43 DAA | |
| --- | --- | --- | --- | --- | --- | --- | --- |
| Penoxsulam + Triclopyr | Imazamox | ECHCG | | BRAPP | | CNPPA | |
| | | Ob | Ex | Ob | Ex | Ob | Ex |
| 327 | 0 | 33 | — | 0 | — | 33 | — |
| 0 | 44 | 78 | — | 61 | — | 0 | — |
| 327 | 44 | 92 | 85 | 90 | 61 | 75 | 33 |

BRAPP = *Brachiaria platyphylla* (GRISEB.) NASH; signalgrass, broadleaf
CNPPA = *Caperonia palustris* ST.-HIL.; Texasweed
ECHCG = *Echinochloa crus-galli*; barnyardgrass
SETSS = *Setaria* spp.; foxtail
Ob = observed value (% control)
Ex = expected, calculated value using Colby Analysis (% control)
DAA = days after application
g ai/ha = grams active ingredient per hectare
g ae/ha = grams acid equivalent per hectare

What is claimed is:

1. A synergistic herbicidal mixture comprising herbicidally active ingredients, wherein the herbicidally active ingredients consist of an herbicidally effective amount of (a) penoxsulam plus triclopyr triethylamine and (b) imazaethapyr ammonium or imazamox ammonium, wherein the weight ratio (ai/ai) of penoxsulam to triclopyr triethylamine is 0.25/2.06, and if (b) is imazaethapyr ammonium the weight ratio (ai/ai) of penoxsulam plus triclopyr triethylamine to imazaethapyr ammonium is 327/70 to 373/70; and if (b) is imazamox ammonium, the weight ratio (ai/ai) of penoxsulam plus triclopyr triethylamine to imazamox ammonium is 327/44.

2. A method of controlling foxtail, barnyardgrass, Texasweed, or signalgrass which comprises foliar application of an herbicidally effective amount of the synergistic herbicidal mixture of claim 1.

3. A method of controlling undesirable vegetation in rice, wheat, barley, oats, rye, sorghum, corn, maize, pastures, grasslands, rangelands, fallowland, turf, IVM and aquatics which comprises contacting the vegetation or the locus thereof with an herbicidally effective amount of the synergistic herbicidal mixture of claim 1.

4. The synergistic herbicidal mixture of claim 1, wherein (b) is imazaethapyr ammonium, further comprising an agriculturally acceptable adjuvant and/or carrier.

5. The synergistic herbicidal mixture of claim 1, wherein (b) is imazamox ammonium, further comprising an agriculturally acceptable adjuvant and/or carrier.

* * * * *